US012758555B2

(12) United States Patent
Deng et al.

(10) Patent No.: US 12,758,555 B2
(45) Date of Patent: Oct. 13, 2026

(54) PHARMACEUTICAL FORMULATIONS

(71) Applicant: ASTRAZENECA AB, Södertälje (SE)

(72) Inventors: Wanding Deng, Shanghai (CN); Ying Fan, Shanghai (CN)

(73) Assignee: AstraZeneca AB, Södertälje (SE)

(*) Notice: Subject to any disclaimer, the term of this patent is extended or adjusted under 35 U.S.C. 154(b) by 269 days.

(21) Appl. No.: 18/458,436

(22) Filed: Aug. 30, 2023

(65) Prior Publication Data

US 2024/0091231 A1 Mar. 21, 2024

(30) Foreign Application Priority Data

Aug. 31, 2022 (WO) ................ PCT/CN2022/116379

(51) Int. Cl.

| | |
|---|---|
| ***A61K 31/519*** | (2006.01) |
| ***A61K 9/20*** | (2006.01) |
| ***A61K 9/28*** | (2006.01) |
| ***A61P 1/16*** | (2006.01) |
| ***A61P 9/00*** | (2006.01) |
| ***A61P 9/04*** | (2006.01) |
| ***A61P 11/00*** | (2006.01) |

(52) U.S. Cl.

CPC .......... *A61K 31/519* (2013.01); *A61K 9/2009* (2013.01); *A61K 9/2013* (2013.01); *A61K 9/2018* (2013.01); *A61K 9/2054* (2013.01); *A61K 9/2826* (2013.01); *A61K 9/284* (2013.01); *A61K 9/2866* (2013.01); *A61P 1/16* (2018.01); *A61P 9/00* (2018.01); *A61P 9/04* (2018.01); *A61P 11/00* (2018.01)

(58) Field of Classification Search

None

See application file for complete search history.

(56) References Cited

U.S. PATENT DOCUMENTS

| | | | | |
|---|---|---|---|---|
| 5,879,706 | A * | 3/1999 | Carter | A61P 31/22 424/464 |
| 6,524,618 | B1 * | 2/2003 | Kumar | A61K 9/2054 514/777 |
| 9,249,087 | B2 | 2/2016 | Kozikowski et al. | |
| 9,616,063 | B2 | 4/2017 | Inghardt et al. | |
| 10,016,430 | B2 | 7/2018 | Inghardt et al. | |
| 2009/0054468 | A1 * | 2/2009 | Eriksson | A61P 25/14 514/263.21 |
| 2010/0076017 | A1 * | 3/2010 | Searle | A61P 33/02 546/171 |
| 2015/0087661 | A1 * | 3/2015 | Tomkinson | A61K 31/519 544/280 |
| 2016/0152623 | A1 * | 6/2016 | Inghardt | A61P 9/10 544/280 |
| 2021/0169866 | A1 * | 6/2021 | Gogniat | A61K 9/1635 |
| 2021/0369707 | A1 * | 12/2021 | Trower | A61K 31/497 |
| 2025/0161223 | A1 * | 5/2025 | Gururajan | A61K 9/2853 |

FOREIGN PATENT DOCUMENTS

| | | | | |
|---|---|---|---|---|
| JP | 6002869 | B1 * | 10/2016 | A61K 47/14 |
| WO | 03089430 | A1 | 10/2003 | |
| WO | 2005037835 | A1 | 4/2005 | |
| WO | WO-2005/051348 | A2 * | 6/2005 | A61K 9/2886 |
| WO | 2006062465 | A1 | 6/2006 | |
| WO | 2007120097 | A1 | 10/2007 | |
| WO | 2007120098 | A1 | 10/2007 | |
| WO | 2007142576 | A1 | 12/2007 | |
| WO | 2007142577 | A1 | 12/2007 | |
| WO | 2009025618 | A1 | 2/2009 | |
| WO | 2012106343 | A2 | 8/2012 | |
| WO | 2013068875 | A1 | 5/2013 | |
| WO | 2016087338 | A1 | 6/2016 | |
| WO | WO-2024/047094 | A1 | 3/2024 | |

OTHER PUBLICATIONS

English translation of Abstract and claims for JP-6002869-B1 (2016).*

Anderson A.C., "The Process of Structure-Based Drug Design," Chemistry and Biology, 2003, vol. 10, pp. 787-797.

"Cardiovascular Diseases (CVDs)," World Health Organization, May 17, 2017, 6 Pages, https://www.who.int/news-room/fact-sheets/detail/cardiovascular-diseases-(cvds).

Forbes L.V., et al., "Potent Reversible Inhibition of Myeloperoxidase by Aromatic Hydroxamates", The Journal of Biological Chemistry, Dec. 20, 2013, vol. 288, No. 51, pp. 36636-36647.

Freshney R.I., "Culture of Animal Cells: A Manual of Basic Technique and Specialized Application," Sixth Edition, Alan R. Liss, Inc., 2010, 5 Pages.

Inghardt T., et al., "Discovery of AZD4831, a Mechanism-Based Irreversible Inhibitor of Myeloperoxidase, As a Potential Treatment for Heart Failure with Preserved Ejection Fraction", Journal of Medicinal Chemistry, vol. 65, No. 17, Aug. 25, 2022, pp. 11485-11496, XP93108430.

International Search Report and Written Opinion for International Application No. PCT/EP2015/077998, mailed Feb. 1, 2016, 9 Pages.

International Search Report and Written Opinion for International Application No. PCT/EP2023/073116, mailed Oct. 4, 2023, 11 Pages.

International Search Report and Written Opinion for International Application No. PCT/EP2023/073764, mailed Dec. 12, 2023, 15 Pages.

Malmquist J., et al., "Imaging Agents for Myeloperoxidase," Journal of Labelled Compounds and Radiopharmaceuticals, 2012, vol. 55, pp. 393-399.

(Continued)

*Primary Examiner* — Sin J Lee

(74) *Attorney, Agent, or Firm* — Choate, Hall & Stewart LLP; Charles E. Lyon; Michael A. Shinall

(57) ABSTRACT

A pharmaceutical formulation which comprises Compound 1, one or more pharmaceutical fillers, one or more pharmaceutical disintegrants, and one or more pharmaceutical lubricant.

14 Claims, 16 Drawing Sheets

(56) References Cited

OTHER PUBLICATIONS

Sirota J.C., et al., "Elevated Serum Uric Acid Levels Are Associated With Non-Alcoholic Fatty Liver Disease Independently of Metabolic Syndrome Features in the United States: Liver Ultrasound Data from the National Health and Nutrition Examination Survey", Metabolism, 2013, 15 pages, vol. 62, No. 3, pp. 392-399, Doi: 10.1016/j.metabol.2012.08.013.

Thiel K.A., "Structure-Aided Drug Design'S Next Generation," Nature Biotechnology, May 2004, vol. 22, No. 5, pp. 513-519.

Tiden A-K., et al., "2-Thioxanthines are Mechanism-Based Inactivators of Myeloperoxidase That Block Oxidative Stress During Inflammation," The Journal of Biological Chemistry, Oct. 28, 2011, vol. 286, No. 43, pp. 37578-37589.

* cited by examiner

Direct compression process of Compound 1 tablets

Compaction Pressure (CP) vs Tensile Strength (TS)

Solid Fraction vs. Compaction Pressure (CP)

Compaction Pressure (CP) vs Tensile Strength (TS)

Solid Fraction vs. Compaction Pressure (CP)

PHARMACEUTICAL FORMULATIONS

RELATED APPLICATIONS

The application claims the benefit of priority to PCT application No. PCT/CN2022/116379, filed on 31 Aug. 2022, which is incorporated herein by reference in its entirety.

FIELD

The present specification relates to a pharmaceutical formulation comprising 1-{2-[(1R)-1-aminoethyl]-4-chlorobenzyl}-2-thioxo-1,2,3,5-tetrahydro-4H-pyrrolo[3,2-d] pyrimidin-4-one (Compound 1). The specification also relates to the use of the formulation in therapy, particularly the treatment of heart failure with preserved ejection fraction (HFpEF) and chronic obstructive pulmonary disease (COPD), as well as methods of treatment involving the administration of the formulation.

BACKGROUND

1-{2-[(1R)-1-aminoethyl]-4-chlorobenzyl}-2-thioxo-1,2,3,5-tetrahydro-4H-pyrrolo[3,2-d]pyrimidin-4-one (Compound 1 (below)) is disclosed in international patent application WO2016/087338

(Compound 1)

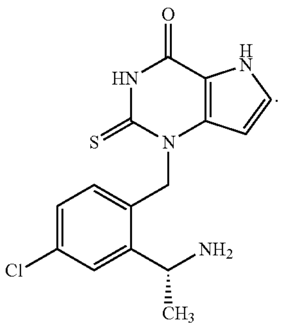

Compound 1 is very adhesive and easily agglomerates into large (0.5-1 mm) particles. A suitable formulation must have good manufacturability (the extent to which a product can be manufactured with relative ease at minimum cost and maximum reliability) because a robust process is needed to deliver product for late-stage clinical trials and commercial purposes. Where the formulation is a tablet, the tablets must achieve a suitable tensile strength, without the need for the application of a high compression force, whilst maintaining an acceptable tablet porosity. These factors minimise the risk of over-compression and variable dissolution rates—a suitable formulation must release its active ingredient in a uniform and acceptable manner. Finally, a formulation for human use must employ pharmaceutically acceptable excipients that meet regulatory requirements for chronic dosing, and must be stable for a meaningful period of time, typically >1 year and ideally up to 3 years.

The present specification describes a pharmaceutical formulation of Compound 1 that satisfies these criteria and is suitable for manufacture on a commercial scale.

DETAILED DESCRIPTION

Many embodiments are detailed throughout the specification and will be apparent to a reader skilled in the art. The specification is not to be interpreted as being limited to any of the recited embodiments.

“A” means “at least one”. In any embodiment where “a” is used to denote a given material or element, “a” may mean one.

“Comprising” means that a given material or element may contain other materials or elements. In any embodiment where “comprising” is mentioned the given material or element may be formed of at least 10% w/w, at least 20% w/w, at least 30% w/w, or at least 40% w/w of the material or element. In any embodiment where “comprising” is mentioned, “comprising” may also mean “consisting of” (or “consists of”) or “consisting essentially of” (or “consists essentially of”) a given material or element.

“Consisting of” or “consists of” means that a given material or element is formed entirely of the material or element. In any embodiment where “consisting of” or “consists of” is mentioned the given material or element may be formed of 100% w/w of the material or element.

“Consisting essentially of” or “consists essentially of” means that a given material or element consists almost entirely of that material or element. In any embodiment where “consisting essentially of” or “consists essentially of” is mentioned the given material or element may be formed of at least 50% w/w, at least 60% w/w, at least 70% w/w, at least 80% w/w, at least 90% w/w, at least 95% w/w or at least 99% w/w of the material or element.

“w/w” means weight by weight.

In any embodiment where “is” or “may be” is used to define a material or element, “is” or “may be” may mean the material or element “consists of” or “consists essentially of” the material or element.

CLAIMS ARE EMBODIMENTS

Compound 1

Compound 1, is 1-{2-[(1R)-1-aminoethyl]-4-chlorobenzyl}-2-thioxo-1,2,3,5-tetrahydro-4H-pyrrolo[3,2-d]pyrimidin-4-one (disclosed in international patent application WO2016/087338)

Compound 1

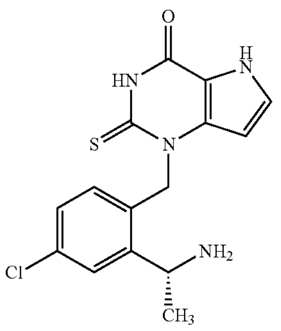

In some embodiments, Compound 1 refers to free base Compound 1.

In some embodiments, Compound 1 refers to a pharmaceutically-acceptable salt of Compound 1.

In some embodiments, the pharmaceutical formulation described herein comprises 1-10% w/w Compound 1.

In some embodiments, the pharmaceutical formulation described herein comprises 10% w/w Compound 1.

In some embodiments, the pharmaceutical formulation described herein comprises 5% w/w Compound 1.

In some embodiments, the pharmaceutical formulation described herein comprises 2.5% w/w Compound 1.

Fillers

In some embodiments, the pharmaceutical formulation described herein comprises one or more pharmaceutically acceptable fillers. In further embodiments, the one or more pharmaceutically acceptable fillers are selected from mannitol, microcrystalline cellulose, and dibasic calcium phosphate anhydrous.

In certain embodiments, the pharmaceutical formulation described herein comprises about 80-95% w/w of one or more pharmaceutically acceptable fillers, including all values and subranges there between, such as, about 80-85% w/w; about 80-90% w/w; about 80-92%; about 82-87% w/w; about 82-90% w/w; about 82-92% w/w; about 82-95% w/w; about 85-87% w/w; about 85-90% w/w; about 85-92% w/w; about 85-95% w/w; about 87-90% w/w; about 87-92% w/w; about 87-95% w/w; about 89-92% w/w; about 89-95% w/w; about 91-93% w/w; about 91-95%, about 83%, about 84%, about 85% w/w, about 86% w/w, about 87% w/w, about 88% w/w, about 89% w/w, about 90% w/w, about 91% w/w, about 92% w/w, about 93% w/w, about 94% w/w, and about 95% w/w.

Mannitol

Mannitol is a polyol (sugar alcohol) with the chemical formula: $C_6H_{14}O_6$. Mannitol can be used as a filler.

In some embodiments, the pharmaceutical formulation described herein comprises mannitol with an average mean particle diameter between about 50 and 300 μm.

In some embodiments, the pharmaceutical formulation described herein comprises mannitol with an average mean particle diameter between about 100 and 200 μm.

In some embodiments, the pharmaceutical formulation described herein comprises mannitol with an average mean particle diameter of about 100 μm.

In some embodiments, the pharmaceutical formulation described herein comprises mannitol with an average mean particle diameter of about 200 μm.

In certain embodiments, the pharmaceutical formulation described herein comprises about 20-75% w/w of mannitol, including all values and subranges there between, such as, 20-30% w/w; 20-40% w/w; 20-50% w/w; 20-60% w/w; 20-70% w/w; 30-40% w/w; 30-50% w/w; 30-60% w/w; 30-75% w/w; 40-50% w/w; 40-60% w/w; 40-75% w/w; 50-60% w/w; 50-75% w/w; 60-75% w/w; and 65-75% w/w.

In certain embodiments, the pharmaceutical formulation described herein comprises about 55% w/w of mannitol. In some embodiments, the pharmaceutical formulation described herein comprises about 55% w/w of mannitol with an average mean particle diameter between about 50 and 300 μm. In some embodiments, the pharmaceutical formulation described herein comprises about 55% w/w of mannitol with an average mean particle diameter between about 100 and 200 μm. In some embodiments, the pharmaceutical formulation described herein comprises about 55% w/w of mannitol with an average mean particle diameter of about 200 μm. In some embodiments, the pharmaceutical formulation described herein comprises about 55% w/w of mannitol with an average mean particle diameter of about 100 μm.

In certain embodiments, the pharmaceutical formulation described herein comprises 55% w/w of mannitol. In some embodiments, the pharmaceutical formulation described herein comprises 55% w/w of mannitol with an average mean particle diameter between about 50 and 300 μm. In some embodiments, the pharmaceutical formulation described herein comprises 55% w/w of mannitol with an average mean particle diameter between about 100 and 200 μm. In some embodiments, the pharmaceutical formulation described herein comprises 55% w/w of mannitol with an average mean particle diameter of about 200 μm. In some embodiments, the pharmaceutical formulation described herein comprises 55% w/w of mannitol with an average mean particle diameter of about 100 μm.

Microcrystalline Cellulose

Microcrystalline cellulose (MCC) can also be used as filler. Microcrystalline cellulose is available in different grades and particle sizes. It may also be referred to as powdered cellulose, cellulose gum or carboxymethylcellulose.

In some embodiments microcrystalline cellulose refers to microcrystalline cellulose with a median particle size of about 40-200 μM.

In some embodiments microcrystalline cellulose refers to microcrystalline cellulose with a median particle size of about 80-120 μM.

In some embodiments microcrystalline cellulose refers to microcrystalline cellulose with a median particle size of about 100 μM.

In some embodiments microcrystalline cellulose refers to Avicel® PH-102 microcrystalline cellulose.

In some embodiments, the pharmaceutical formulation described herein comprises 20-50% w/w microcrystalline cellulose.

In some embodiments, the pharmaceutical formulation described herein comprises 30-40% w/w microcrystalline cellulose.

In some embodiments, the pharmaceutical formulation described herein comprises 30-36% w/w microcrystalline cellulose.

In some embodiments, the pharmaceutical formulation described herein comprises 33-34% w/w microcrystalline cellulose.

In some embodiments, the pharmaceutical formulation described herein comprises about 33.5% w/w microcrystalline cellulose.

In some embodiments, the pharmaceutical formulation described herein comprises 33.5% w/w microcrystalline cellulose.

In some embodiments microcrystalline cellulose refers to cellulose, microcrystalline of European Pharmacopoeial standard.

In some embodiments microcrystalline cellulose refers to microcrystalline cellulose of Japanese Pharmacopoeial standard.

In some embodiments microcrystalline cellulose refers to microcrystalline cellulose of United States Pharmacopoeial standard.

Dibasic Calcium Phosphate Anhydrous (DCPA)

Dibasic calcium phosphate anhydrous (DCPA) has the chemical formula: $CaHPO_4$. DCPA can be used as a water insoluble filler. DCPA is also known as calcium hydrogen phosphate and phosphoric acid calcium salt (1:1).

In some embodiments, the pharmaceutical formulation described herein comprises about 5-40% w/w anhydrous dibasic calcium phosphate.

In some embodiments, the pharmaceutical formulation described herein comprises about 5-15% w/w anhydrous dibasic calcium phosphate.

In some embodiments, the pharmaceutical formulation described herein comprises about 10% w/w anhydrous dibasic calcium phosphate.

In some embodiments, the pharmaceutical formulation described herein comprises about 20-30% w/w anhydrous dibasic calcium phosphate.

In some embodiments, the pharmaceutical formulation described herein comprises about 25% w/w anhydrous dibasic calcium phosphate.

In some embodiments, the pharmaceutical formulation described herein comprises about 30-40% w/w anhydrous dibasic calcium phosphate.

In some embodiments, the pharmaceutical formulation described herein comprises about 36.5% w/w anhydrous dibasic calcium phosphate.

In some embodiments, the pharmaceutical formulation described herein comprises 36.5% w/w anhydrous dibasic calcium phosphate.

In some embodiments dibasic calcium phosphate anhydrous refers to dibasic calcium phosphate anhydrous of European Pharmacopoeial standard.

In some embodiments dibasic calcium phosphate refers anhydrous to dibasic calcium phosphate anhydrous of Japanese Pharmacopoeial standard.

In some embodiments dibasic calcium phosphate anhydrous refers to dibasic calcium phosphate anhydrous of United States Pharmacopoeial standard.

Disintegrants

In some embodiments, the pharmaceutical formulation described herein comprises one or more pharmaceutically acceptable disintegrants.

In some embodiments, the pharmaceutical formulation described herein comprises one or more pharmaceutically acceptable disintegrants selected from croscarmellose sodium and low substituted hydroxypropyl cellulose.

In some embodiments, the pharmaceutical formulation described herein comprises croscarmellose sodium.

In some embodiments, the pharmaceutical formulation described herein comprises low substituted hydroxypropyl cellulose.

Croscarmellose Sodium

Croscarmellose sodium, or sodium CMC, is a cross-linked polymer of carboxymethylcellulose sodium.

In some embodiments, the pharmaceutical formulation described herein comprises 1-10% w/w croscarmellose sodium.

In some embodiments, the pharmaceutical formulation described herein comprises 3-5% w/w croscarmellose sodium.

In some embodiments, the pharmaceutical formulation described herein comprises about 4% w/w croscarmellose sodium.

In some embodiments, the pharmaceutical formulation described herein comprises 4% w/w croscarmellose sodium.

Low-Substituted Hydroxypropyl Cellulose

Hydroxypropyl cellulose (HPC) is an ether of cellulose in which some of the hydroxyl groups in the repeating glucose units have been hydroxypropylated forming—$OCH_2CH(OH)CH_3$ groups. L-HPC is a low-substituted hydroxypropyl ether of cellulose within a small portion of the hydroxypropyl groups in the glucose unit. Typically, L-HPC has a molar substitution of 0.2-0.4. L-HPC is available in various grades, including LH-11, LH-21, LH-22, LH-31, and LH-B1.

In some embodiments, the pharmaceutical formulation described herein comprises 5-20% w/w low substituted hydroxypropyl cellulose.

In some embodiments, the pharmaceutical formulation described herein comprises 7.5-12.5% w/w low substituted hydroxypropyl cellulose.

In some embodiments, the pharmaceutical formulation described herein comprises about 10% w/w low substituted hydroxypropyl cellulose.

In some embodiments, the pharmaceutical formulation described herein comprises 10% w/w low substituted hydroxypropyl cellulose.

In some embodiments, the low substituted hydroxypropyl cellulose is LH-21 grade low substituted hydroxypropyl cellulose.

In some embodiments, the low substituted hydroxypropyl cellulose is LH-31 grade low substituted hydroxypropyl cellulose.

In some embodiments, the low substituted hydroxypropyl cellulose is LH-B1 grade low substituted hydroxypropyl cellulose.

In some embodiments low substituted hydroxypropyl cellulose refers to hydroxypropyl cellulose, low-substituted of European Pharmacopoeial standard.

In some embodiments low substituted hydroxypropyl cellulose refers to low-substituted hydroxypropyl cellulose of National Formulary standard.

In some embodiments low substituted hydroxypropyl cellulose refers to low substituted hydroxypropyl cellulose of Japanese Pharmacopoeial standard.

Lubricants

Magnesium Stearate

Magnesium stearate has the formula $Mg(C_{18}H_{35}O_2)_2$. It is used as a lubricant to reduce friction and is typically a white, water-insoluble powder.

In some embodiments, the pharmaceutical formulation described herein comprises 1-3% w/w magnesium stearate.

In some embodiments, the pharmaceutical formulation described herein comprises about 2% w/w magnesium stearate.

In some embodiments, the pharmaceutical formulation described herein comprises 2% w/w magnesium stearate.

In some embodiments magnesium stearate refers to magnesium stearate of United States Pharmacopoeial standard.

In some embodiments magnesium stearate refers to magnesium stearate of British Pharmacopoeial standard.

In some embodiments magnesium stearate refers to magnesium stearate of European Pharmacopoeial standard.

In some embodiments magnesium stearate refers to magnesium stearate of Japanese Pharmacopoeial standard.

In some embodiments magnesium stearate refers to magnesium stearate of Chinese Pharmacopoeial standard.

Pharmacopoeia

Herein where pharmacopeia standards are mentioned, it is to be understood that the standards are as published in the following editions of the pharmacopoeias:

TABLE 1

| Pharmacopeia Editions | |
|---|---|
| Pharmacopoeia | Edition |
| United States Pharmacopoeia | 43 |
| British Pharmacopoeia | 2020 Edition |
| European Pharmacopoeia | $10^{th}$ Edition |
| Japanese Pharmacopoeia | $17^{th}$ Edition |
| Chinese Pharmacopoeia | 2020 Edition |
| National Formulary | 38 |

Tablet

In some embodiments, the pharmaceutical formulation described herein may be a tablet.

In some embodiments, the pharmaceutical formulation described herein may be a tablet for oral administration.

In some embodiments, the pharmaceutical formulation described herein may be an immediate release tablet.

In some embodiments, the pharmaceutical formulation described herein may be administered daily.

In some embodiments, the pharmaceutical formulation described herein may be a tablet administered daily.

In some embodiments, the pharmaceutical formulation described herein may be administered orally.

In some embodiments, the pharmaceutical formulation described herein may be a tablet administered orally.

In some embodiments, the pharmaceutical formulation described herein may comprise 1 to 10 mg of Compound 1.

In some embodiments, the pharmaceutical formulation described herein may comprise 10 mg of Compound 1.

In some embodiments, the pharmaceutical formulation described herein may comprise 5 mg of Compound 1.

In some embodiments, the pharmaceutical formulation described herein may comprise 2.5 mg of Compound 1.

In some embodiments, the pharmaceutical formulation described herein may be a tablet comprising 2.5 mg of Compound 1.

In some embodiments, the pharmaceutical formulation described herein may be a tablet comprising 5 mg of Compound 1.

In some embodiments, the pharmaceutical formulation described herein may be a tablet comprising 10 mg of Compound 1.

In some embodiments, the pharmaceutical formulation described herein may comprise:

About 2.5% w/w Compound 1
About 55% w/w mannitol
About 36.5% w/w microcrystalline cellulose
About 4% w/w croscarmellose sodium
About 2% w/w magnesium stearate.

In some embodiments, the pharmaceutical formulation described herein may comprise:

About 2.5% w/w Compound 1
About 55% w/w mannitol
About 36.5% microcrystalline cellulose
About 4% w/w croscarmellose sodium
About 2% magnesium stearate.

In some embodiments, the pharmaceutical formulation described herein may comprise:

1-10% w/w Compound 1;
45-60% w/w mannitol;
30-40% w/w microcrystalline cellulose;
3-5% w/w croscarmellose sodium; and
1-3% w/w magnesium stearate.

In some embodiments, the pharmaceutical formulation described herein may comprise: 2.5% w/w Compound 1;

55% w/w mannitol;
36.5% w/w microcrystalline cellulose;
4% w/w croscarmellose sodium; and
2% w/w magnesium stearate.

In some embodiments, the pharmaceutical formulation described herein may comprise:

2.5% w/w Compound 1;
55% w/w mannitol having an average mean particle diameter of about 100 μm;
36.5% w/w microcrystalline cellulose having a median particle size of about 100 μM;
4% w/w croscarmellose sodium; and
2% w/w magnesium stearate.

In some embodiments, the pharmaceutical formulation described herein may comprise:

2.5 mg Compound 1;
55 mg mannitol;
36.5 mg microcrystalline cellulose;
is 4.0 mg croscarmellose sodium; and
2.0 mg magnesium stearate.

In some embodiments, the pharmaceutical formulation described herein may comprise:

5.0 mg Compound 1;
110.0 mg mannitol;
73.0 mg microcrystalline cellulose;
8.0 mg croscarmellose sodium; and
4.0 mg magnesium stearate.

Coatings

In some embodiments, where the pharmaceutical formulation is in the form of a tablet, it may be advantageous to coat the tablet with a coating. The resultant coated tablet would then comprise a tablet core and a coating. A coated tablet may assist a patient in swallowing a tablet. A coloured coating may assist with patient compliance and/or differentiation from other medicines, particularly those administered as part of a combination treatment.

In some embodiments, the pharmaceutical formulation described herein may be a coated tablet. If the tablet is a coated tablet it is to be understood that any % w/w value quoted herein refers to the w/w composition of the tablet core.

In some embodiments, the pharmaceutical formulation described herein may be a colour coated tablet.

In some embodiments, the pharmaceutical formulation described herein may be a film-coated tablet.

In some embodiments, the pharmaceutical formulation described herein may be a tablet coated with a film-coating comprising a film forming polymer. In further embodiments, the film forming polymer is selected from hydroxypropyl methylcellulose (hypromellose, HPMC), hydroxypropyl cellulose (HPC), polyvinylpyrrolidone (PVP), polyvinylpolypyrrolidone (PVPP), and mixtures thereof. In further embodiments, the film forming polymer is selected from HPMC, HPC, and mixtures thereof. In still further embodiments, the film forming polymer is HPMC.

In still further embodiments, the film-coating further comprises a pigment, such as titanium dioxide, iron oxide yellow, iron oxide red, ferrosoferric oxide, and mixtures thereof.

In some embodiments, the pharmaceutical formulation described herein may be a coloured film-coated tablet.

In some embodiments, the pharmaceutical formulation described herein may be a white film-coated tablet.

In some embodiments, the pharmaceutical formulation described herein may be an orange film-coated tablet.

In some embodiments, the coating is present at about 1.5-4.5% w/w, including all values and subranges there between, including about 1.5-3.5% w/w, 1.5-2.5% w/w, 2-4% w/w, 2-3% w/w, 2.5-4.5% w/w, 2.5-3.5% w/w, 3-4% w/w, 2.4% w/w, 2.5% w/w, 2.6% w/w, 2.7%, 2.8% w/w, 2.9% w/w, 3% w/w, 3.1% w/w, 3.2% w/w, 3.3% w/w, 3.4% w/w, 3.5% w/w, 3.6% w/w, 3.7% w/w, 3.9% w/w, 3.9% w/w, and 4% w/w.

Method of Treatment

Prophylaxis of diseases or conditions in which modulation of the activity of the enzyme myeloperoxidase (MPO) is desirable. In particular, linkage of MPO activity to disease has been implicated in numerous diseases, including diseases with inflammatory, cardiovascular, and/or neurodegenerative components, as well as neutrophilic driven diseases.

In some embodiments there is provided a pharmaceutical formulation as disclosed herein, for use in a method of treatment of the human or animal body by therapy.

In some embodiments there is provided a method of treating diseases or conditions in which modulation of the activity of the enzyme myeloperoxidase (MPO) is desirable in a warm-blooded animal, such as man, which comprises administering to said animal an effective amount of a pharmaceutical formulation described herein.

In some embodiments there is provided a method of treating diseases or conditions in which inhibition of the activity of the enzyme myeloperoxidase (MPO) is desirable in a warm-blooded animal, such as man, which comprises administering to said animal an effective amount of a pharmaceutical formulation described herein.

In some embodiments there is provided a method of treating diseases or conditions with inflammatory, cardiovascular, and/or neurological components, and/or neutrophilic driven diseases in a warm-blooded animal, such as man, which comprises administering to said animal an effective amount of a pharmaceutical formulation described herein.

In some embodiments there is provided a method of treating autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, and/or type 2 diabetes in a warm-blooded animal, such as man, which comprises administering to said animal an effective amount of a pharmaceutical formulation described herein.

In some embodiments there is provided a method of treating coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and/or chemotherapy-induced cardiotoxicity in a warm-blooded animal, such as man, which comprises administering to said animal an effective amount of a pharmaceutical formulation described herein.

In some embodiments there is provided a method of treating Alzheimer's disease, Parkinson's disease, stroke, multiple sclerosis (MS), multiple system atrophy (MSA), amyotrophic lateral sclerosis (ALS), and/or epilepsy in a warm-blooded animal, such as man, which comprises administering to said animal an effective amount of a pharmaceutical formulation described herein.

In some embodiments there is provided a method of treating heart failure, heart failure with reduced ejection fraction, heart failure with preserved ejection fraction, non-alcoholic steatohepatitis (NASH), or chronic obstructive pulmonary disease (COPD) in a warm-blooded animal, such as man, which comprises administering to said animal an effective amount of a pharmaceutical formulation described herein.

In some embodiments, there is provided a pharmaceutical formulation as described herein comprising Compound 1 for use as a medicament.

In some embodiments there is provided a pharmaceutical formulation as described herein, for use in therapy.

In some embodiments, there is provided the use of a pharmaceutical formulation as described herein, in the manufacture of a medicament for treating diseases or conditions in which modulation of the activity of the enzyme myeloperoxidase (MPO) is desirable.

In some embodiments, there is provided the use of a pharmaceutical formulation as described herein, in the manufacture of a medicament for treating diseases or conditions in which inhibition of the activity of the enzyme myeloperoxidase (MPO) is desirable.

In some embodiments there is provided the use of a pharmaceutical formulation as described herein, in the manufacture of a medicament for use in treating diseases or conditions with inflammatory, cardiovascular, and/or neurological components, and/or neutrophilic driven diseases.

In some embodiments there is provided the use of a pharmaceutical formulation as described herein, in the manufacture of a medicament for use in the treatment of autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, or type 2 diabetes.

In some embodiments there is provided the use of a pharmaceutical formulation, as described herein, in the manufacture of a medicament for use in the treatment of coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and/or chemotherapy-induced cardiotoxicity.

In some embodiments there is provided the use of a pharmaceutical formulation, as described herein, in the manufacture of a medicament for use in the treatment of Alzheimer's disease, Parkinson's disease, stroke, multiple sclerosis (MS), multiple system atrophy (MSA), amyotrophic lateral sclerosis (ALS), and/or epilepsy.

In some embodiments there is provided the use of a pharmaceutical formulation as described herein, in the manufacture of a medicament for the treatment of heart failure, heart failure with reduced ejection fraction, heart failure with preserved ejection fraction, non-alcoholic steatohepatitis (NASH), or chronic obstructive pulmonary disease (COPD), in a warm-blooded animal such as man.

In some embodiments there is provided the use of a pharmaceutical formulation as described herein, for use in the treatment of diseases or conditions in which modulation of the activity of the enzyme myeloperoxidase (MPO) is desirable.

In some embodiments there is provided the use of a pharmaceutical formulation as described herein, for use in the treatment of diseases or conditions in which inhibition of the activity of the enzyme myeloperoxidase (MPO) is desirable.

In some embodiments there is provided the use of a pharmaceutical formulation as described herein, for use in the treatment of diseases or conditions with inflammatory, cardiovascular, and/or neurological components, and/or neutrophilic driven diseases.

In some embodiments there is provided the use of a pharmaceutical formulation as described herein, for use in the treatment of autoimmune diseases, chronic kidney disease (CKD), acute kidney injury (AKI), renal glomerular damage, nephritis, glomerulonephritis, interstitial nephritis, tubulointerstitial nephritis, diabetic nephropathy, cardiorenal syndrome (CRS), non-alcoholic steatohepatitis (NASH), non-alcoholic fatty liver disease (NAFLD), inflammatory bowel disease (IBD), Crohn's disease, colitis, ulcerative colitis, irritable bowel syndrome (IBS), rheumatoid arthritis, systemic lupus erythematosus, liver steatosis, liver fibrosis, gout, sickle cell disease, cystic fibrosis, vasculitis, anti-neutrophilic cytoplasmic autoantibody (ANCA)-associated vasculitis, asthma, chronic obstructive pulmonary disease (COPD), non-cystic fibrosis bronchiectasis (NCFB), vascular dysfunction, lipoprotein modification, or type 2 diabetes.

In some embodiments there is provided the use of a pharmaceutical formulation as described herein, for use in the treatment of coronary artery disease, acute coronary syndrome, heart failure, heart failure with reduced ejection fraction (HFrEF), heart failure with preserved ejection fraction (HFpEF), arrhythmia, cardiomyopathy, dilated cardiomyopathy, hypertrophic cardiomyopathy myocardial infarction, hypertension, pulmonary arterial hypertension (PAH), pulmonary hypertension, vascular dysfunction, atherosclerosis, ischemic heart disease, atrial fibrillation, pericarditis, diastolic dysfunction, atherosclerotic plaque rupture, abdominal aortic aneurysm, and/or chemotherapy-induced cardiotoxicity.

In some embodiments there is provided the use of a pharmaceutical formulation as described herein, for use in the treatment of Alzheimer's disease, Parkinson's disease, stroke, multiple sclerosis (MS), multiple system atrophy (MSA), amyotrophic lateral sclerosis (ALS), and/or epilepsy.

In some embodiments there is provided the use of a pharmaceutical formulation as described herein, for use in the treatment of heart failure, heart failure with reduced ejection fraction, heart failure with preserved ejection fraction, non-alcoholic steatohepatitis (NASH), or chronic obstructive pulmonary disease (COPD)

As used herein, the terms "treatment" and "treat" refer to reversing, alleviating, delaying the onset of, or inhibiting the progress of a disease or disorder, or one or more symptoms thereof, as described herein. In some embodiments, treatment may be conducted after one or more symptoms have developed. In other embodiments, treatment may be conducted in the absence of symptoms. For example, treatment may be conducted to a susceptible individual prior to the onset of symptoms (e.g. in light of a history of symptoms and/or in light of genetic or other susceptibility factors). Treatment may also be continued after symptoms have resolved, for example to present or delay their recurrence.

DETAILED DESCRIPTION OF THE FIGURES

FIG. 1 depicts the direct compression process described herein.

FIG. 2A compares the Compaction Pressure (CP) vs. Tensile Strength of Variants 1, 2, 3, and 14.

FIG. 2B compares the Solid Fraction vs. Compaction Pressure (CP) of Variants 1, 2, 3, and 14.

FIG. 2C compares the Solid Fraction vs. Tensile Strength (TS) of Variants 1, 2, 3, and 14.

FIG. 3A compares the Compaction Pressure (CP) vs. Tensile Strength of Variants 5 and 10

FIG. 3B compares the Solid Fraction vs. Compaction Pressure (CP) of Variants 5 and 10.

FIG. 3C compares the Solid Fraction vs. Tensile Strength (TS) of Variants 5 and 10.

FIG. 4A compares the Compaction Pressure (CP) vs. Tensile Strength of Variants 3, 7 and 11.

FIG. 4B compares the Solid Fraction vs. Compaction Pressure (CP) of Variants 3, 7 and 11.

FIG. 4C compares the Solid Fraction vs. Tensile Strength (TS) of Variants 3, 7 and 11.

FIG. 5A compares the Compaction Pressure (CP) vs. Tensile Strength of Variants 9 and 12.

FIG. 5B compares the Solid Fraction vs. Compaction Pressure (CP) of Variants 9 and 12.

FIG. 5C compares the Solid Fraction vs. Tensile Strength (TS) of Variants 9 and 12.

FIG. 6 compares the dissolution profiles of Variants 1, 2, and 3.

FIG. 7 compares the dissolution profiles of Variants 5 and 10.

FIG. 8 compares the dissolution profiles of Variants 3, 11, and 15.

FIG. 9 compares the dissolution profiles of Variants 9, 12, and 15.

Figure 12:
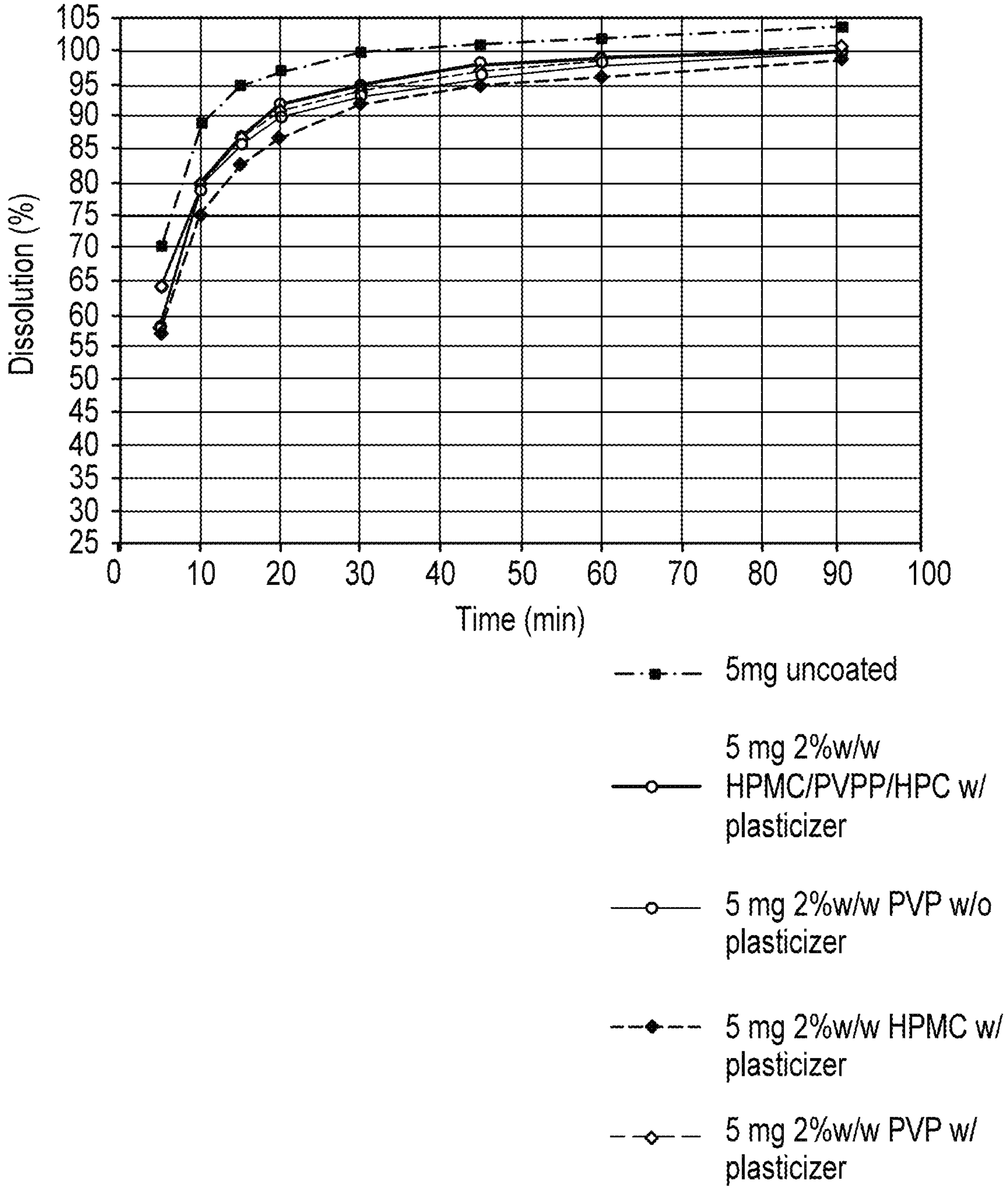

FIG. 12 compares the dissolution profile of various film coated tablets coated at 2% w/w.

Figure 13:
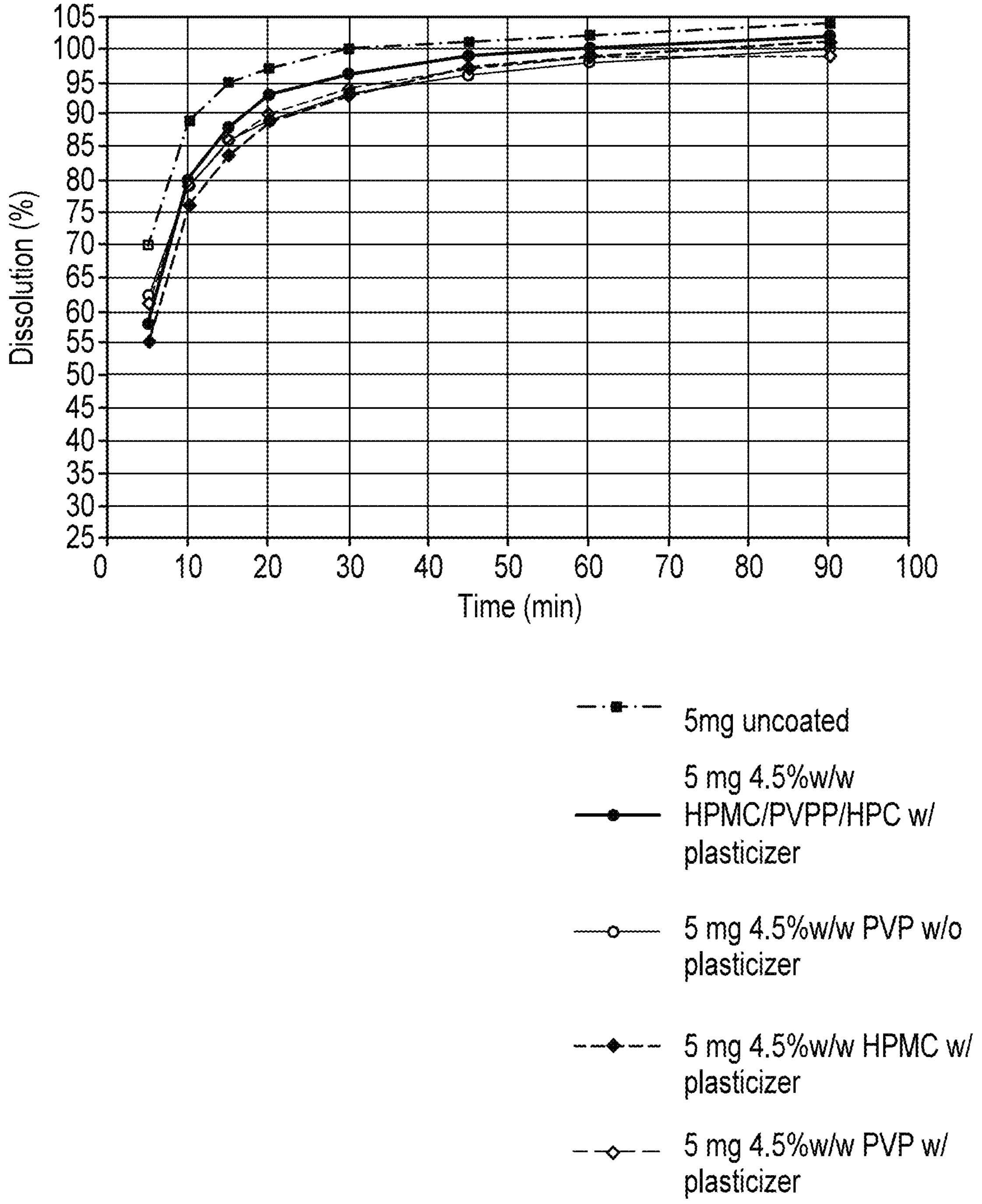

FIG. 13 compares the dissolution profile of various film coated tablets coated at 4.5% w/w.

Figure 14:
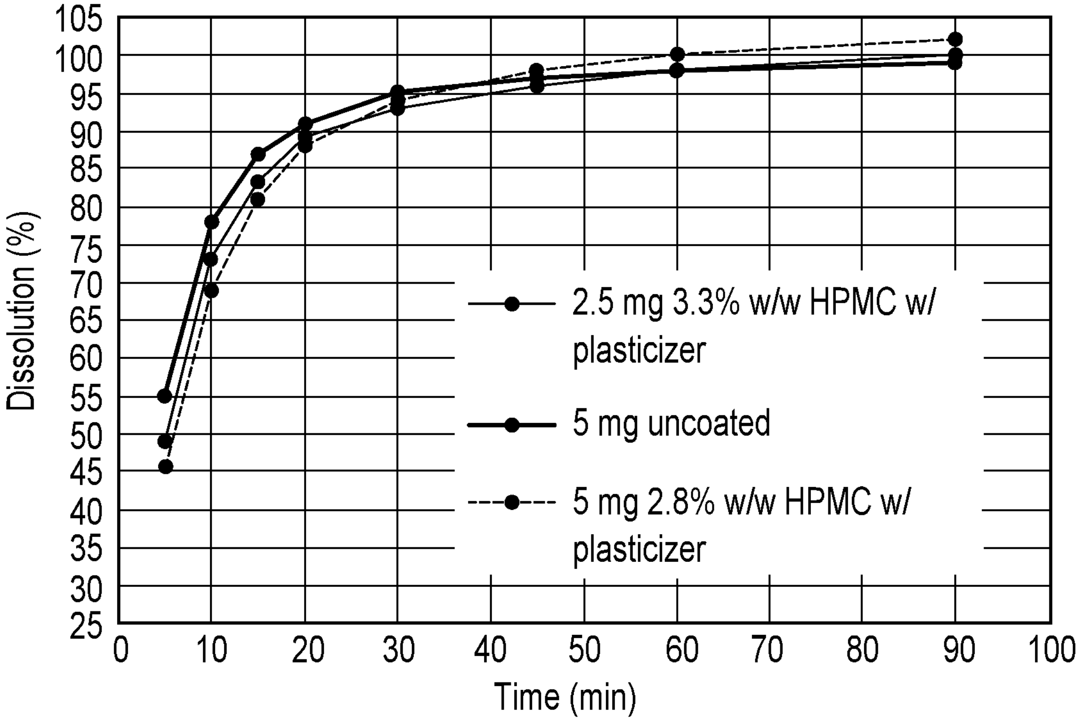

FIG. 14 compares the dissolution profile of coated and uncoated tablets comprising 2.5 mg Compound 1 or 5 mg Compound 1.

EXAMPLES

Compound 1 was produced by the synthesis route disclosed in WO2016/087338. The excipients used in the Example and Results sections are shown in Table 2.

TABLE 2

| Excipients, abbreviations and grades | | | |
|---|---|---|---|
| Excipient name | Abbrevia-tion | Grades | /Supplier |
| Mannitol | — | Pearlitol 100SD Pearlitol 200SD | Roquette |
| Microcrystalline cellulose | MCC | Avicel PH102 | DuPont |
| Dicalcium phosphate anhydrous | DCPA | Emcompress ® | JRS Pharma |
| Low-substituted hydroxypropyl cellulose | L-HPC | LH-31 LH-21 LH-B1 | Shinetsu |
| Crosscarmellose Sodium | — | Ac-Di-Sol | DuPont |
| Magnesium stearate | — | Ligamed MF-2-V | Peter Greven |

Example 1: Manufacture of Tablets

Tablets of Compound 1 as described herein were manufactured using a dry process with direct compression.

Figure 1:
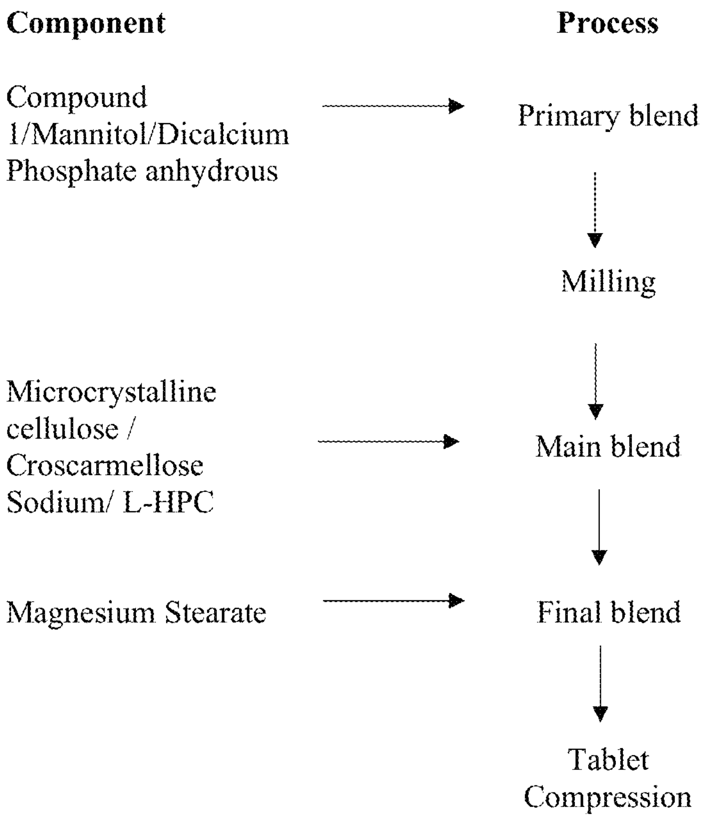
Figure 2A:
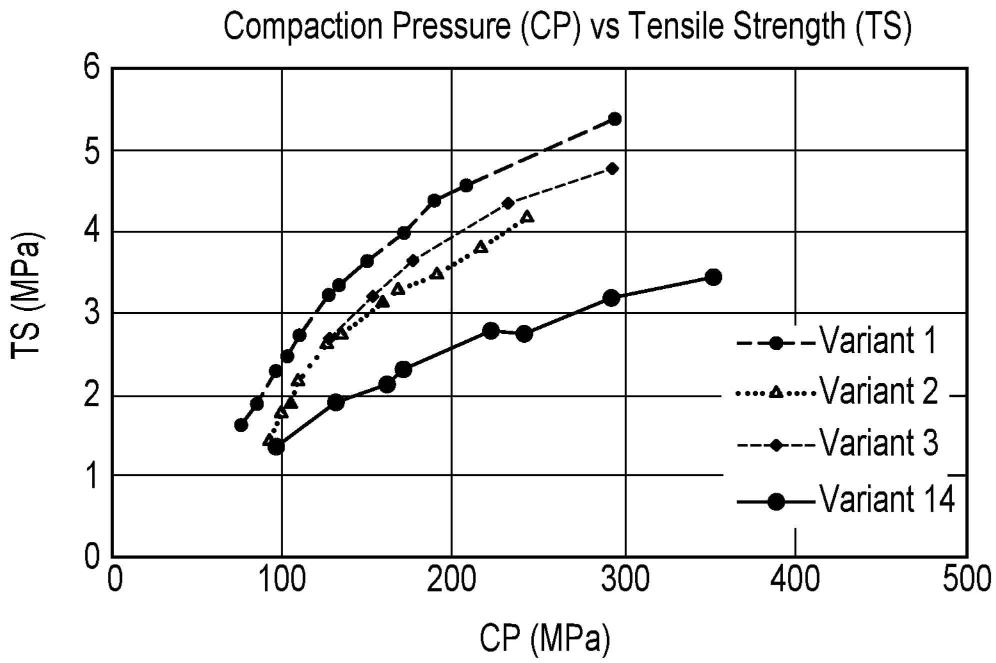
Figure 2B:
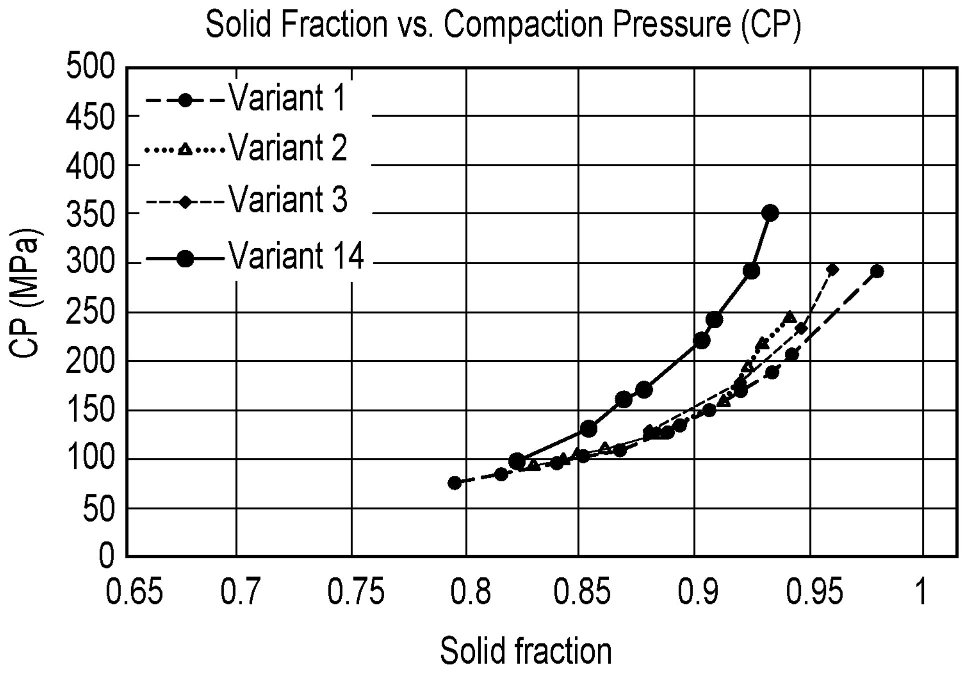
Figure 2C:
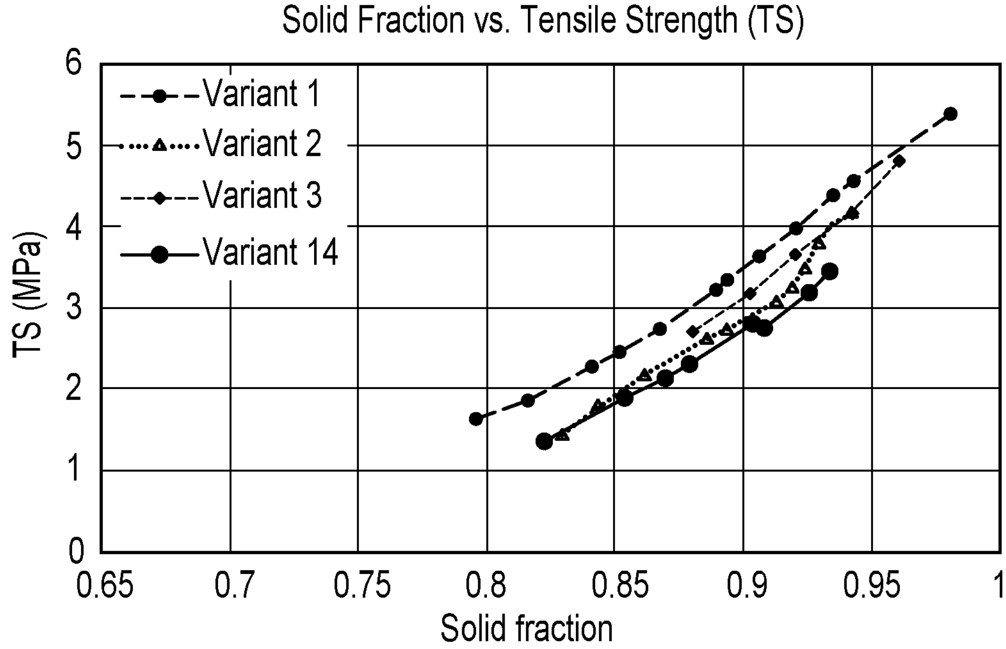
Figure 3A:
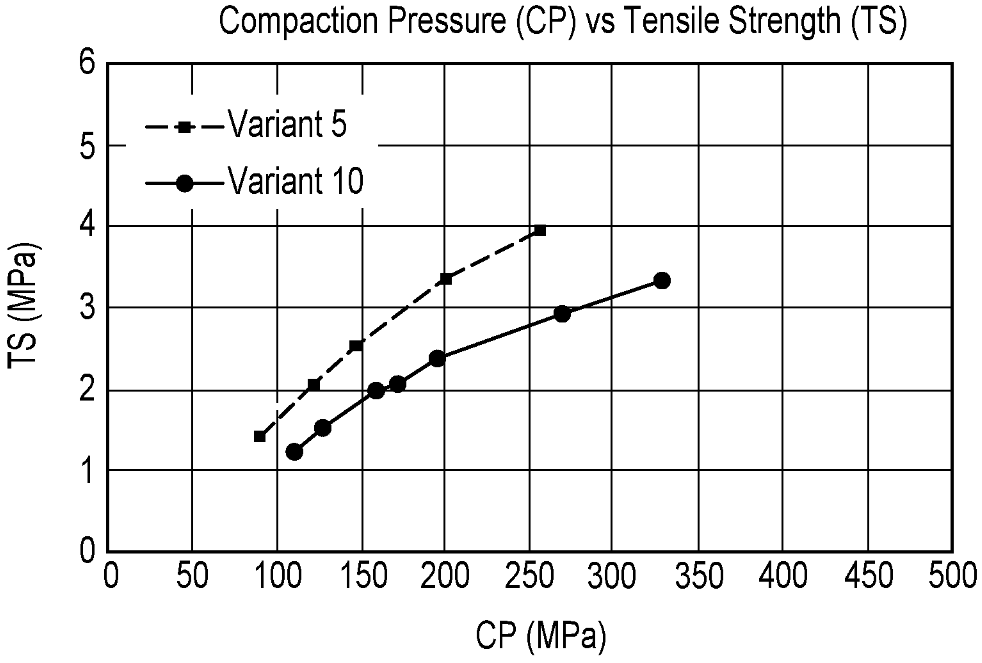
Figure 3B:
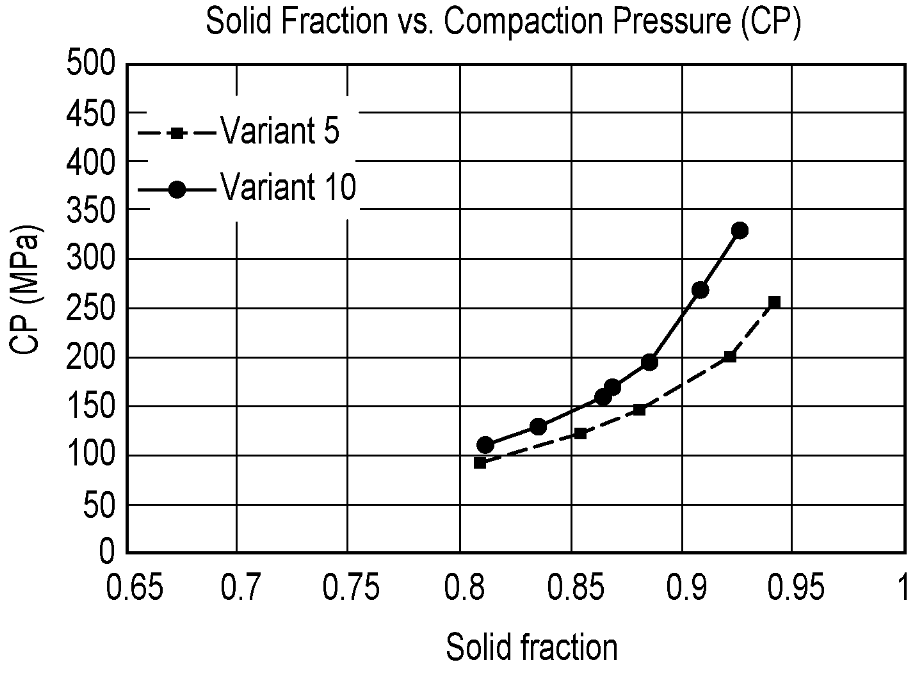
Figure 3C:
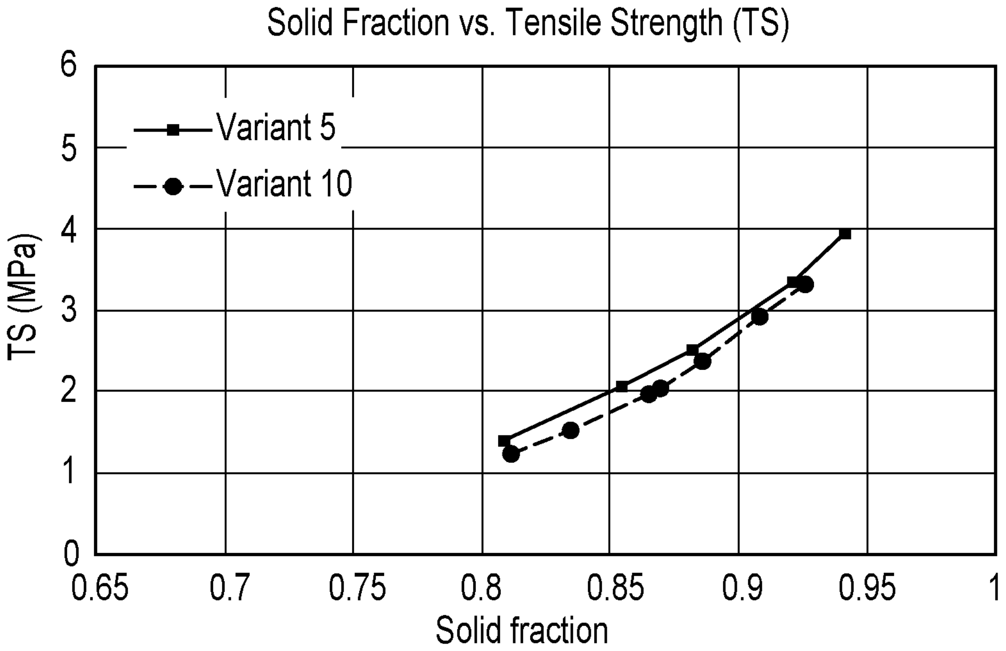
Figure 4A:
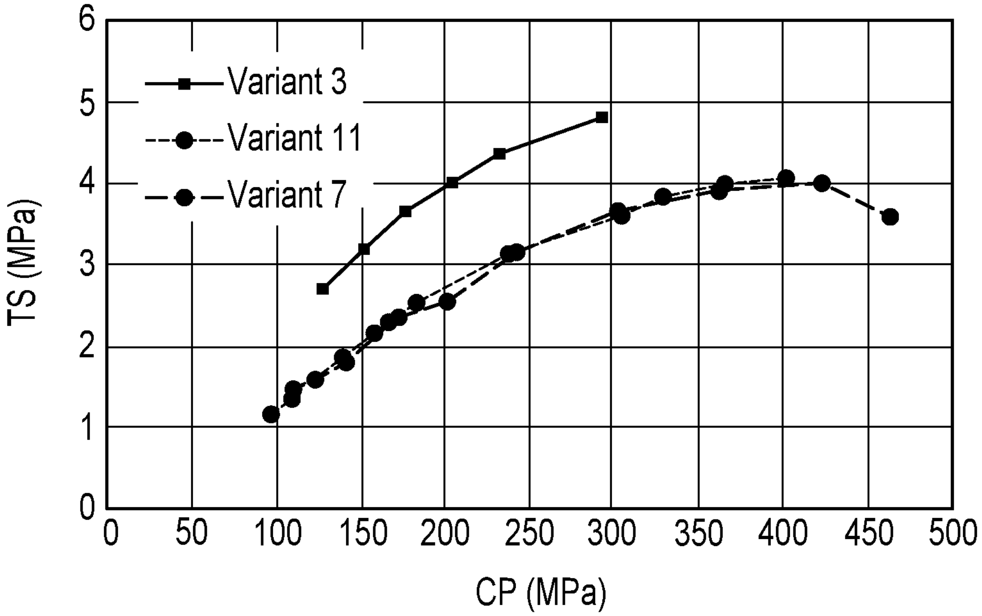
Figure 4B:
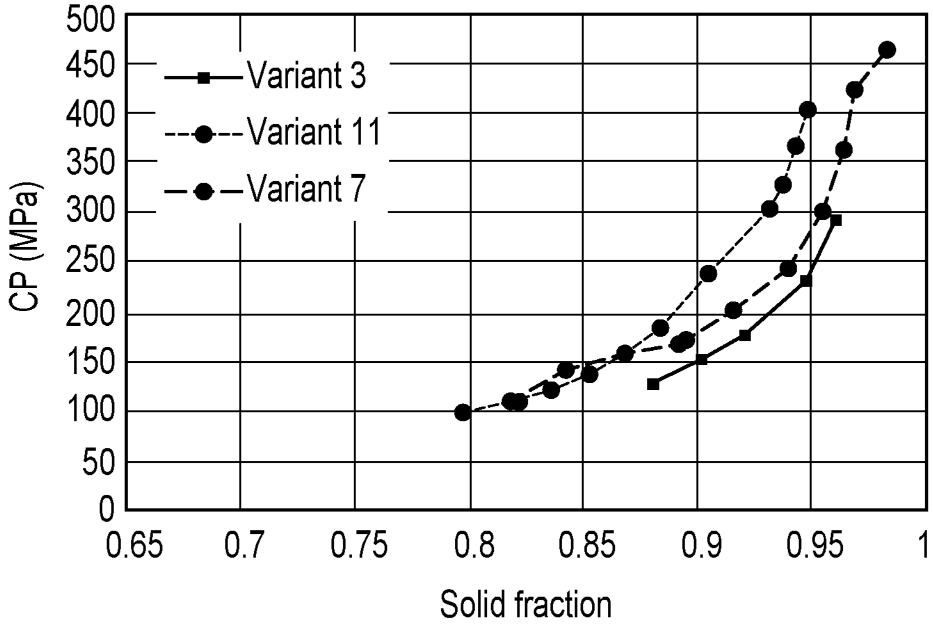
Figure 4C:
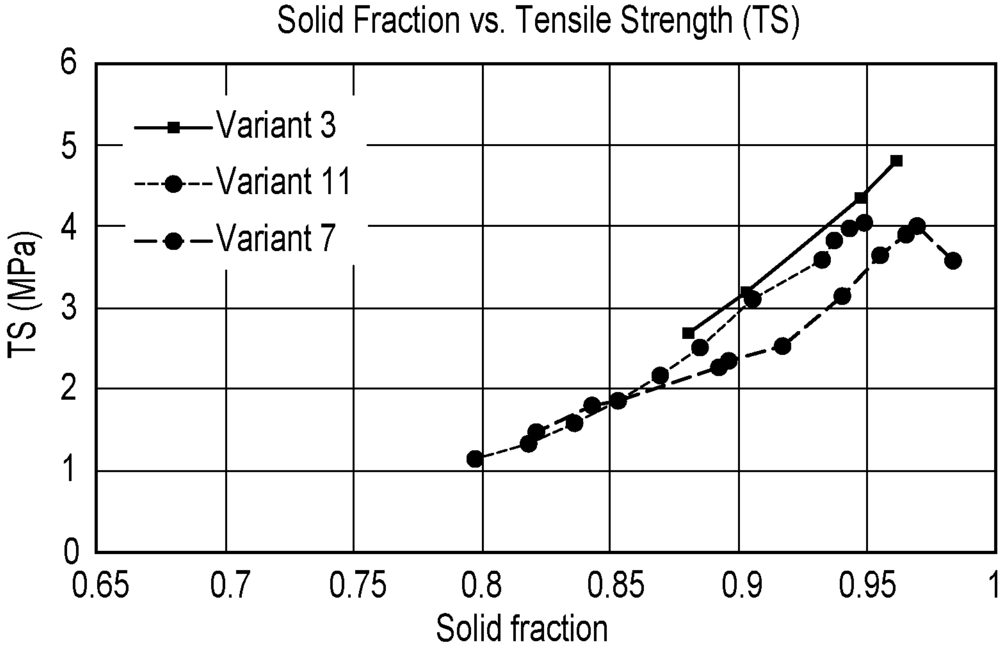
Figure 5A:
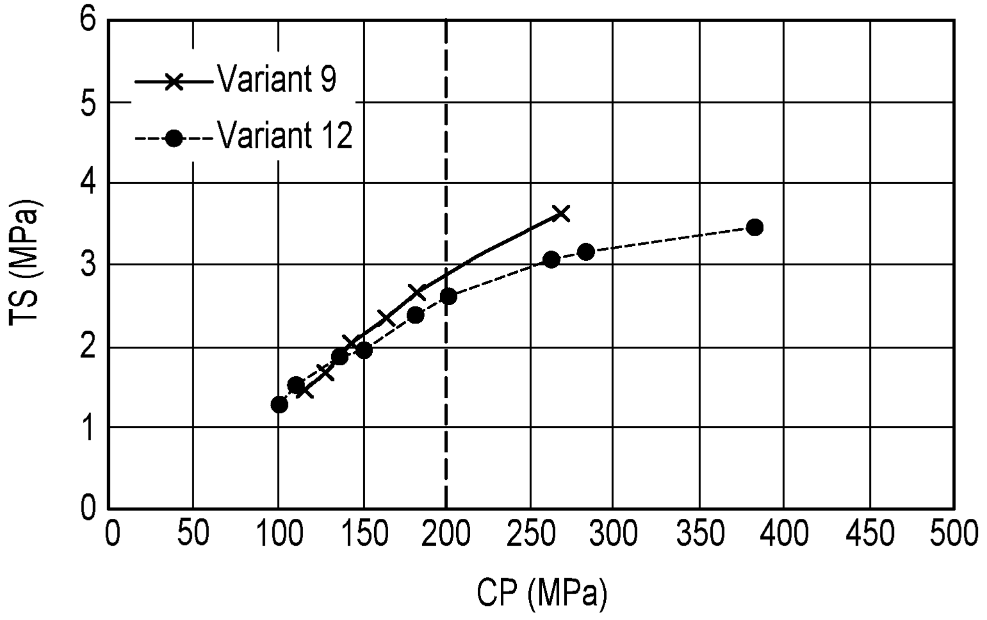
Figure 5B:
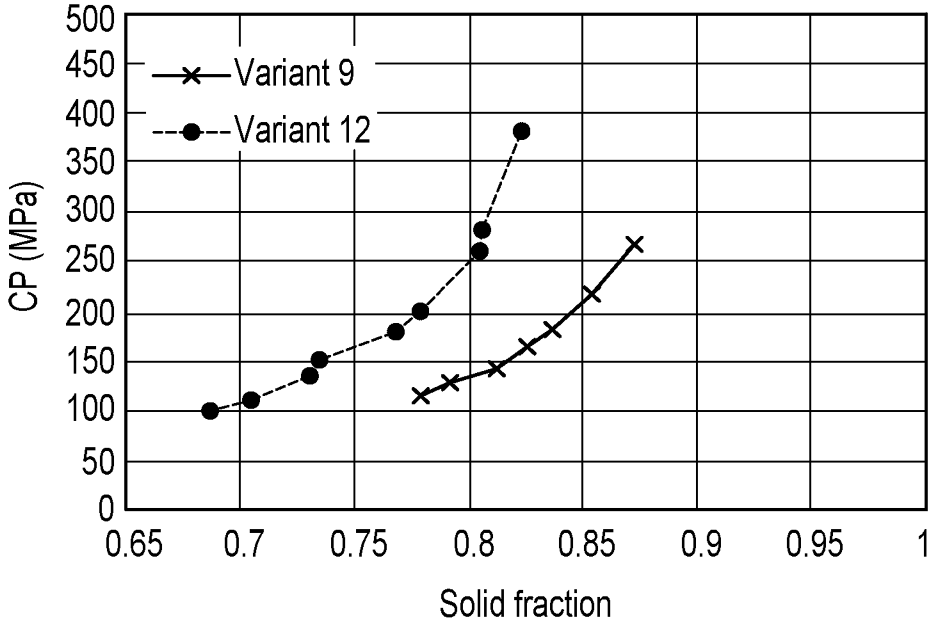
Figure 5C:
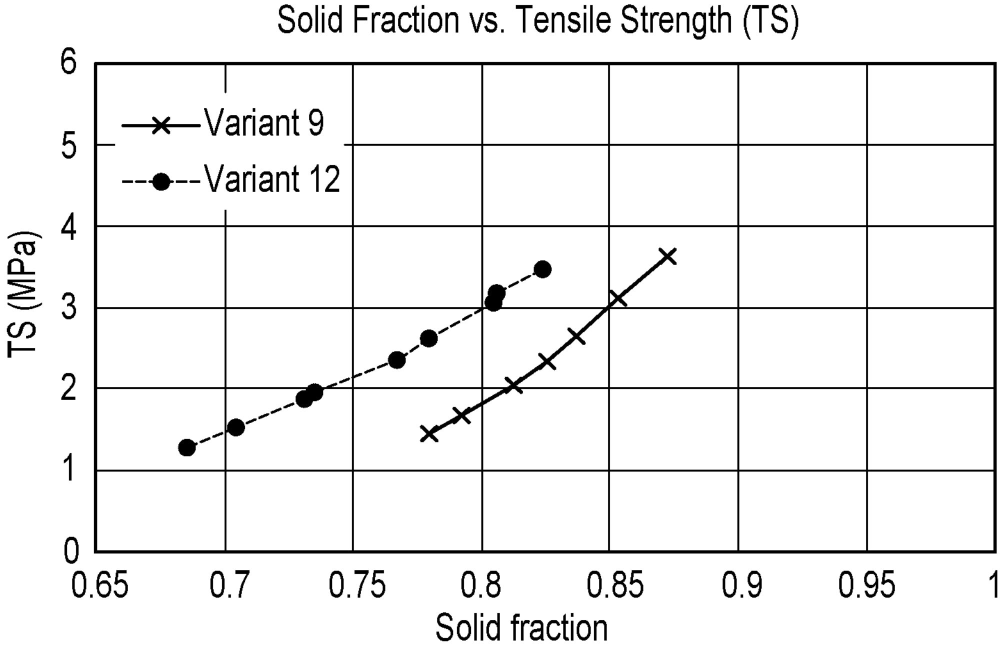
Figure 6:
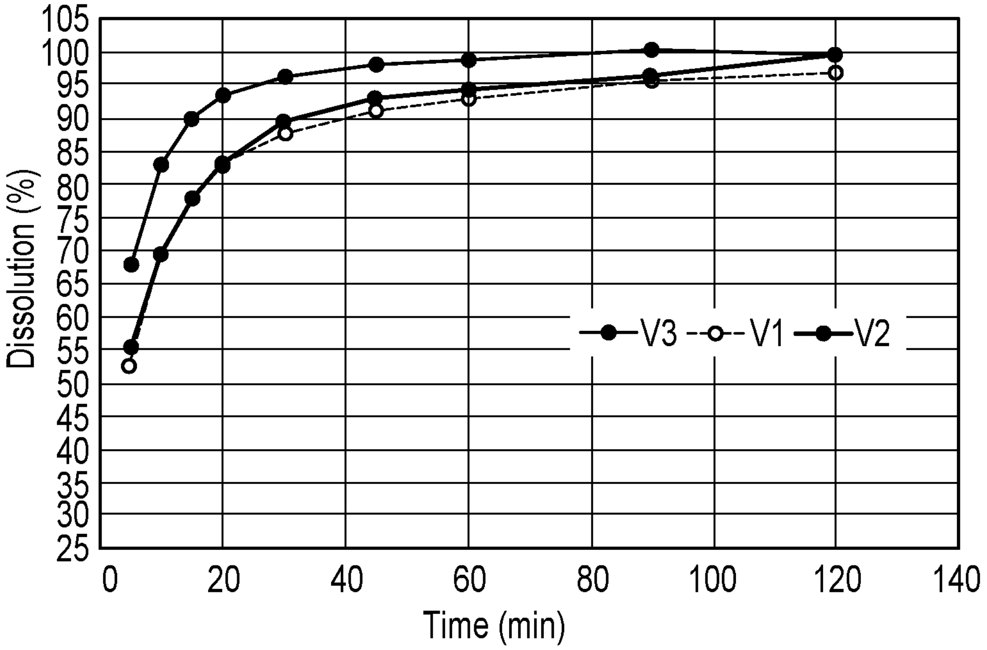
Figure 7:
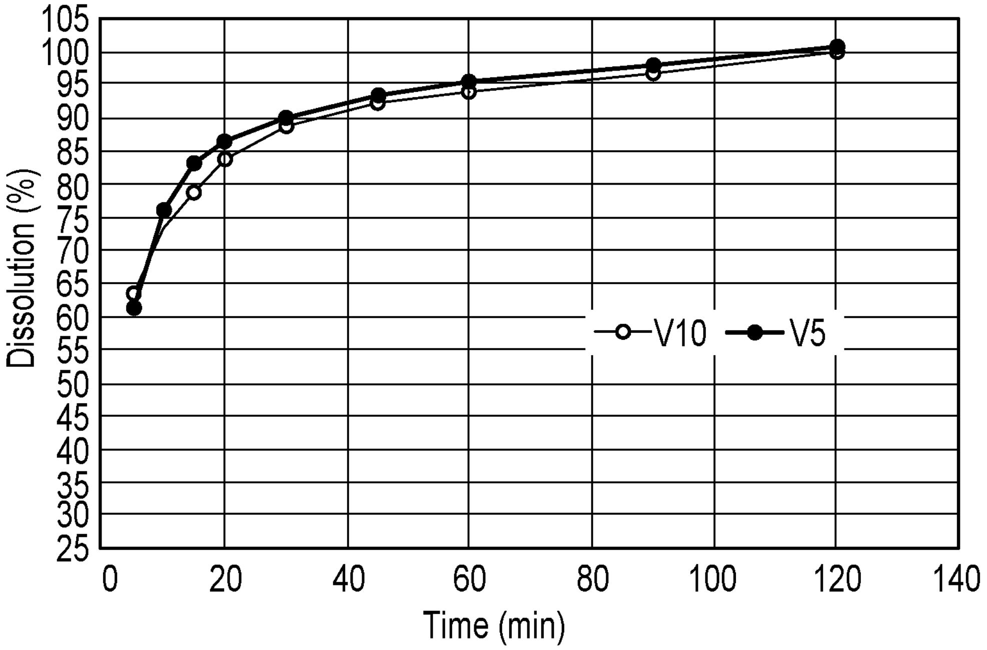
Figure 8:
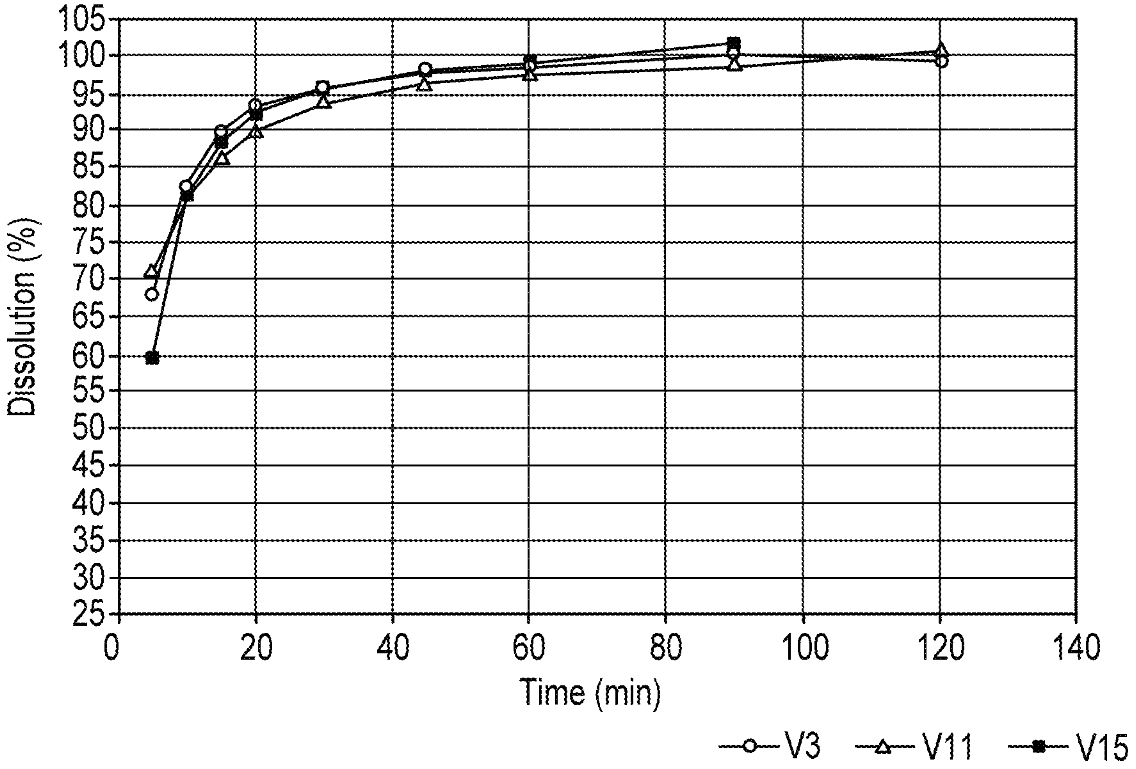
Figure 9:
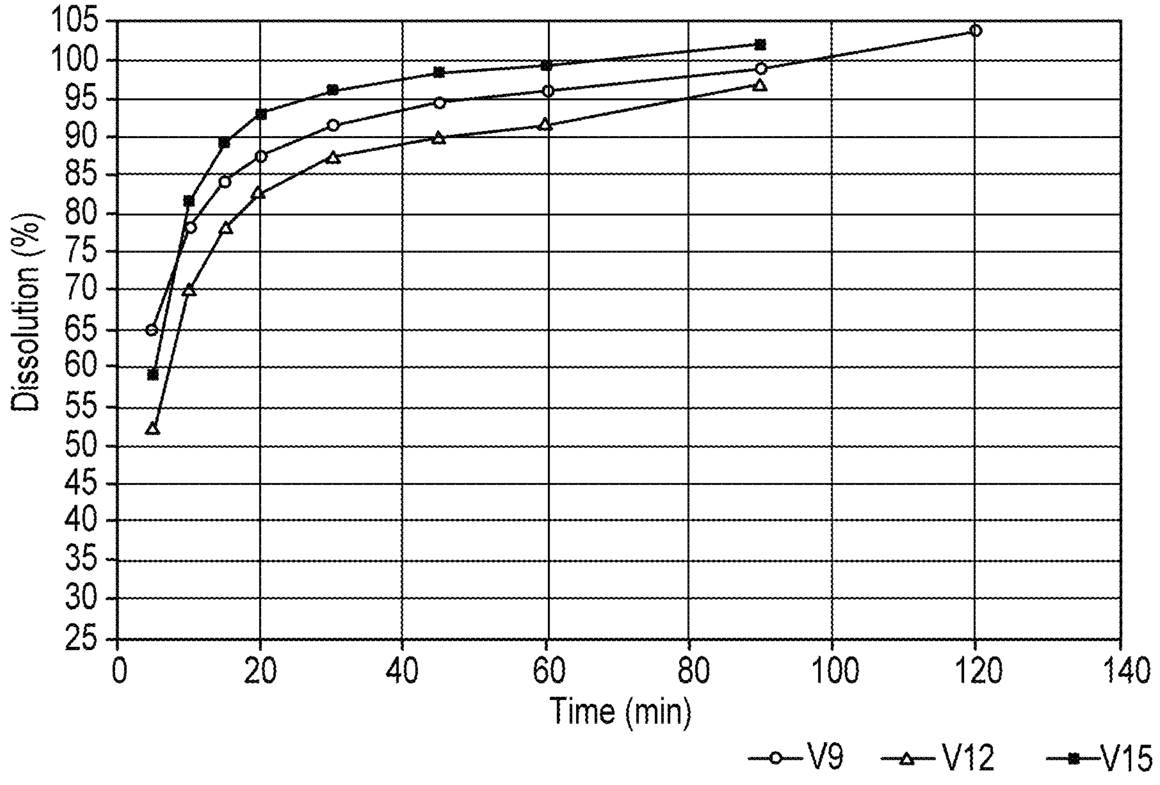

The formulations described in Tables 3-A and 3-B were prepared according (or analogous) to the procedure described below at a 1 kg scale and summarized in FIG. 1. The values quoted in the table are % w/w.

1. Compound 1 was blended with mannitol, and if present, DCPA, in a ERWEKA DKM (Double Cone Mixer), 11 L blender at approximately 200 revolutions at a speed of 20 rpm.
2. The resulting powder blend from step 1 was sieved through a 600 μm screen at approximately 500 rpm milling speed on a Frewitt mill CW-150.
3. The milled powder blend was subsequently blended with MCC, L-HPC, and/or croscarmellose sodium in in a ERWEKA DKM (Double Cone Mixer), 11 L blender at approximately 200 revolutions at a speed of 20 rpm.
4. The resulting blend from step 3 was subsequently blended with magnesium stearate in in a ERWEKA DKM (Double Cone Mixer), 11 L blender at approximately 200 revolutions at a speed of 20 rpm.
5. The tablet compression was performed on a Korsch XL-100 with appropriately sized oval or round tooling to prepare 400 mg (10 mg Compound 1), 200 mg (5 mg Compound 1), and 100 mg (2.5 mg Compound 1) tablets.

TABLE 3-A

| | Var. 1 | Var. 2 | Var. 3 | Var. 4* | Var. 5 | Var. 6* | Var. 7 | Var. 8* |
|---|---|---|---|---|---|---|---|---|
| Tablet Strength/mg | 10 | 10 | 10 | 10 | 10 | 10 | 10 | 10 |
| Compound 1 | 2.5 | 2.5 | 2.5 | 2.5 | 2.5 | 2.5 | 5.0 | 2.5 |
| Fillers | | | | | | | | |
| Mannitol, Pearlitol 100SD | 35.0 | 35.0 | 37.5 | 43.0 | 60.0 | 73.0 | 70.5 | *** |
| Mannitol, Pearlitol 200SD | *** | *** | *** | *** | *** | *** | *** | 73.0 |
| Dicalcium phosphate anhydrous (DCPA), Emcompass | *** | *** | *** | *** | *** | *** | *** | *** |
| Microcrystalline cellulose, Avicel PH102 | 50.5 | 50.5 | 54.0 | 42.5 | 25.5 | 13.0 | 18.5 | 12.5 |
| Disintegrants | | | | | | | | |
| Low-substituted hydroxypropyl cellulose, LH-31 | 10.0 | *** | *** | 10.0 | 10.0 | 10.0 | *** | *** |
| Low-substituted hydroxypropyl cellulose, LH-21 | *** | 10.0 | *** | *** | *** | *** | *** | *** |
| Low-substituted hydroxypropyl cellulose, LH-B1 | *** | *** | *** | *** | *** | *** | *** | 10.0 |
| Croscarmellose Sodium | *** | *** | 4.0 | *** | *** | *** | 4.0 | *** |
| Lubricant | | | | | | | | |
| Magnesium Stearate | 2.0 | 2.0 | 2.0 | 2.0 | 2.0 | 1.5 | 2.0 | 2.0 |

*not executed

TABLE 3-B

| | Var. 9 | Var. 10 | Var. 11A | Var. 11B | Var. 12 | Var. 13 | Var. 14 | Var. 15 | Var. 16 |
|---|---|---|---|---|---|---|---|---|---|
| Tablet Strength/mg | 10 | 10 | 10 | 10 | 5 | 10 | 10 | 5 | 5 |
| Compound 1 | 2.5 | 2.5 | 2.5 | 2.5 | 2.5 | 5.0 | 5.0 | 2.5 | 2.5 |
| Fillers | | | | | | | | | |
| Mannitol, Pearlitol 100SD | 60.0 | 73.0 | 73.0 | 73.0 | *** | 53.0 | 58.0 | 55.0 | 60.0 |
| Mannitol, Pearlitol 200SD | *** | *** | *** | *** | *** | *** | *** | *** | *** |

TABLE 3-B-continued

| | Var. 9 | Var. 10 | Var. 11A | Var. 11B | Var. 12 | Var. 13 | Var. 14 | Var. 15 | Var. 16 |
|---|---|---|---|---|---|---|---|---|---|
| Dicalcium phosphate anhydrous, Emcompass | 10.0 | *** | *** | *** | 36.5 | *** | *** | *** | *** |
| Microcrystalline cellulose, Avicel PH102 | 15.5 | 12.5 | 18.5 | 18.5 | 55.0 | 36.0 | 25.0 | 36.5 | 25.5 |
| Disintegrants | | | | | | | | | |
| Low-substituted hydroxypropyl cellulose, LH-31 | 10.0 | *** | *** | *** | *** | *** | *** | *** | *** |
| Low-substituted hydroxypropyl cellulose, LH-21 | *** | *** | *** | *** | *** | *** | *** | *** | *** |
| Low-substituted hydroxypropyl cellulose, LH-B1 | *** | 10.0 | *** | *** | *** | *** | 10.0 | *** | 10.0 |
| Croscarmellose Sodium | *** | *** | 4.0 | 4.0 | 4.0 | 4.0 | *** | 4.0 | *** |
| Lubricant | | | | | | | | | |
| Magnesium Stearate | 2.0 | 2.0 | 2.0 | 2.0 | 2.0 | 2.0 | 2.0 | 2.0 | 2.0 |

Example 2: Testing of Tablets

Compression Profile

All batches were compressed separately using a suitable rotary tablet press (e.g. Korsch XL 100) with the same punch design (round 6 mm for 2.5 mg strength; round 8 mm for 5 mg strength and oval 14 mm×7 mm for 10 mg strength) under different compression forces. Breaking force and thickness of the produced tablets were characterized using suitable hardness and thickness measurement equipment. Tensile strength was calculated in terms of breaking force and dimension of produce tablets. The results are presented in FIGS. 2-5.

The compression profile depicts the tablet tensile strength as a function of the applied compaction force for all batches. This profile is normalised for the punch tip face area and tablet geometry, allowing for a true comparison of formulation robustness independent of tablet size.

Dissolution Profiles

The dissolution profiles of the tablets were performed in accordance with the United States Pharmacopeia and the European Pharmacopoeia, using Apparatus II (paddle apparatus) with a stirring speed of 75 rpm in a pH 6.1 sodium phosphate (0.075 μM)/citric acid (0.025 μM) buffer. Concentration of Compound 1 is quantified by comparison of the UV response at 290 nm with a background correction at 400 nm of the dissolution sample with that of an external reference standard solution.

Dissolution profiles of the tablets were measured in pH6.1 USP medium with method 2. FIGS. 6-9 compare dissolution profiles of various formulations.

Example 3: Coating

Figure 10A:
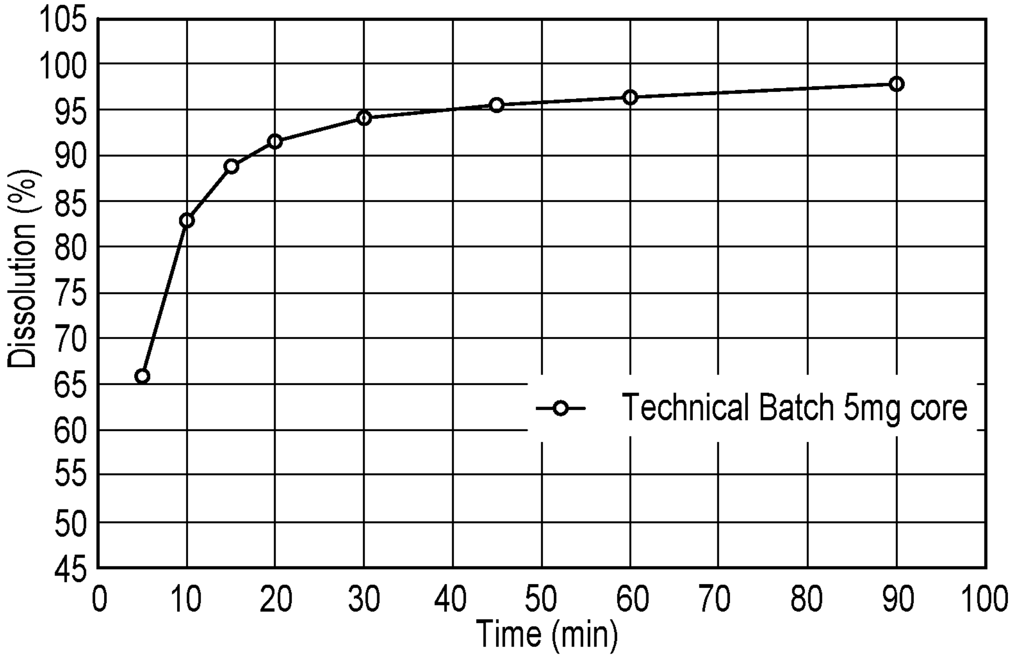
FIGS. 10A and 10B depict the dissolution profiles of Variant 15 before and after coating.
Figure 10B:
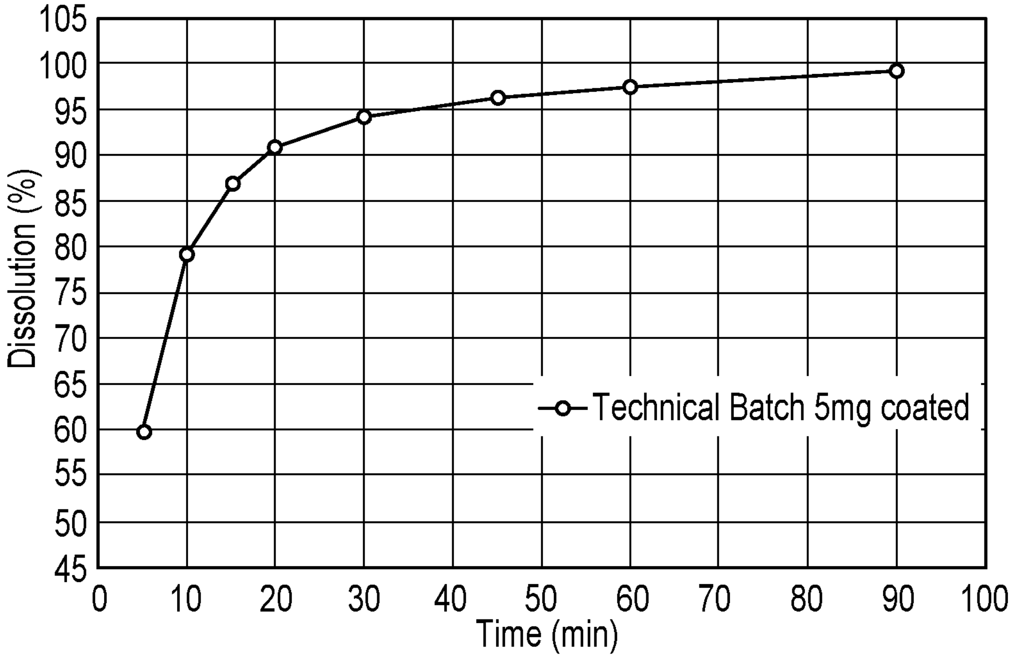
Figure 11:
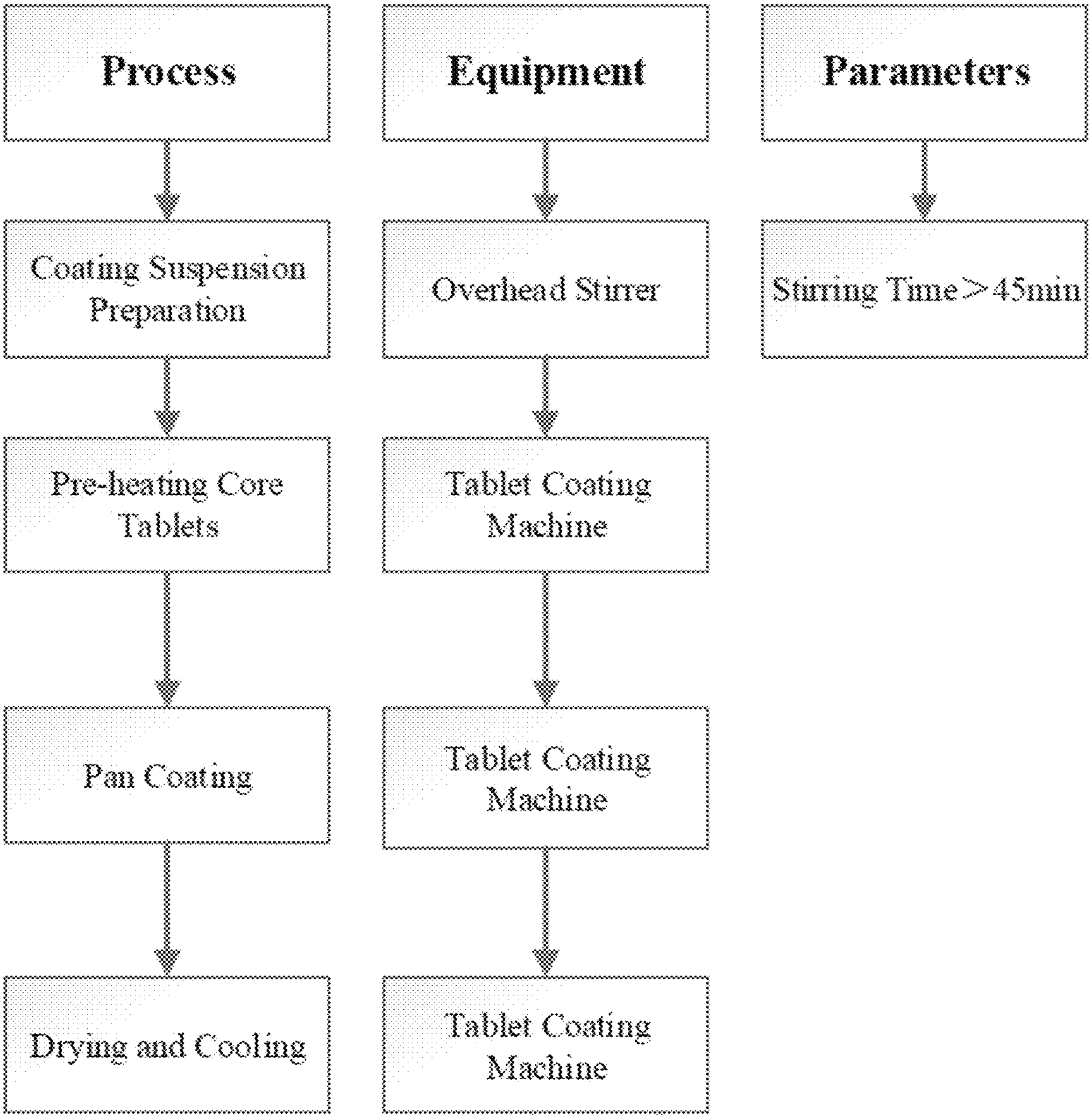
FIG. 11 depicts the coating process described herein.

Tablets with the Variant 15 formulation comprising 2.5 mg of Compound 1 and 5 mg of Compound 1 were film-coated using standard pan coating techniques as shown in FIG. 11 with a HPMC/HPC coating (Aquarius Prime White, BKN318005, Ashland) for a weight gain of 3.5% w/w of the uncoated tablet for the 5 mg tablet and 3.5% w/w of the uncoated tablet for the 2.5 mg tablet. The dissolution profile of the 5 mg coated tablet was measured in pH 6.1 USP medium with method 2 as described in Example 2. FIGS. 10A and 10B depict the dissolution profiles of the uncoated and coated tablet respectively.

Tablets comprising 2.5 mg Compound 1 (100 mg total weight, herein after "2.5 mg core tablets") and 5 mg Compound 1 (200 mg total weight, herein after "5 mg core tablets") having the composition of described in Table 4 were prepared according to Example 1.

TABLE 4

| Component | w/w % |
|---|---|
| Compound 1 | 2.5 |
| Mannitol, Pearlitol 100SD | 55 |
| Microcrystalline cellulose, Avicel PH102 | 36.5 |
| Croscarmellose Sodium | 4 |
| Magnesium Stearate | 2 |

The 5 mg core tablets were film-coated using standard pan coating techniques as shown in FIG. 11 with aqueous suspensions of the proprietary coatings listed in Table 5 for weight gains of 2% or 4.5% w/w.

TABLE 5

| Main Polymer(s) | Coating | Conc. %(w/w) | Manufacturer |
|---|---|---|---|
| HPMC, PVPP, HPC (with plasticizer) | Aquarius ™ Preferred HSP BON313109 Orange | 20 | Ashland |
| PVA (no plasticizer) | Opadry ™ 85A630003-CN Orange | 20 | Colorcon |
| HPMC (with plasticizer) | Opadry ™ 03K630008-CN Orange | 15 | Colorcon |
| PVA (with plasticizer) | Opadry ™ II 85F630054-CN Orange | 20 | Colorcon |

Dissolution profiles of the tablets were measured in pH 6.1 USP medium with method 2 as described in Example 2. FIGS. 12 and 13 compare dissolution profiles of the 2% w/w coatings and 4.5% coatings respectively.

The 2.5 mg core tablets were coated with Opadry 03K630008-CN Orange for a weight gain of 3.3% and the 5 mg core tablets were coated with Opadry 03K630008-CN Orange for a weight gain of 2.8%. Dissolution profiles of the tablets were measured in pH 6.1 USP medium with method 2 as described in Example 2 and the results are shown in FIG. 14.

All references cited herein, including patents, patent applications, papers, text books, and the like, and the references cited therein, to the extent that they are not already, are hereby incorporated herein by reference in their entirety for all purposes.

The invention claimed is:

1. A pharmaceutical formulation comprising Compound 1, or a pharmaceutically acceptable salt thereof, mannitol, microcrystalline cellulose, croscarmellose sodium, and magnesium stearate, wherein Compound 1 is 1-{2-[(1R)-1-aminoethyl]-4-chlorobenzyl}-2-thioxo-1,2,3,5-tetrahydro-4H-pyrrolo [3,2-d]pyrimidin-4-one (Compound 1)

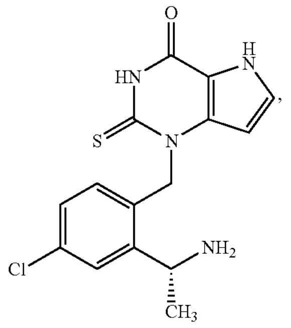

wherein Compound 1 is present at about 2.5% w/w, the mannitol is present at about 55% w/w, the microcrystalline cellulose is present at about 36.5% w/w, the croscarmellose sodium is present at about 4% w/w, and the magnesium stearate is present at about 2% w/w, wherein the weight percentages are based on the total weight of the pharmaceutical formulation.

2. The pharmaceutical formulation of claim 1 wherein the mannitol has an average mean particle diameter of about 100 μm.

3. The pharmaceutical formulation of claim 1, wherein the microcrystalline cellulose has a median particle size of about 100 μm.

4. The pharmaceutical formulation of claim 1 comprising 2.5 mg of Compound 1.

5. The pharmaceutical formulation of claim 1 comprising 5 mg of Compound 1.

6. The pharmaceutical formulation of claim 1 wherein the pharmaceutical formulation is a tablet.

7. The pharmaceutical formulation of claim 6, wherein the tablet further comprises a film-coating.

8. The pharmaceutical formulation of claim 7 wherein the film-coating comprises a polymer, wherein the polymer is hydroxypropyl methylcellulose (HPMC), hydroxypropyl cellulose (HPC), polyvinylpyrrolidone (PVP), polyvinylpolypyrrolidone (PVPP), or mixtures thereof.

9. The pharmaceutical formulation of claim 8 wherein the film-coating comprises HPMC.

10. The pharmaceutical formulation of claim 7 wherein the film-coating is present at about 2.5-3.5% w/w of the coated tablet.

11. A method of treating, or reducing a risk of, a disease or condition in which inhibition of the enzyme MPO is beneficial which comprises administering to a person suffering from or at risk of, said disease or condition, a pharmaceutical formulation of claim 1.

12. The method according to claim 11, wherein said disease or condition is heart failure, heart failure with reduced ejection fraction, heart failure with preserved ejection fraction, non-alcoholic steatohepatitis (NASH), or chronic obstructive pulmonary disease (COPD).

13. The pharmaceutical formulation of claim 1 comprising between 1 mg and 10 mg of Compound 1.

14. The pharmaceutical formulation of claim 1 comprising 10 mg of Compound 1.

* * * * *